(12) United States Patent
Allard et al.

(10) Patent No.: US 6,375,936 B1
(45) Date of Patent: Apr. 23, 2002

(54) PHOTOPROTECTIVE COSMETIC COMPOSITION CONTAINING AN ANIONIC SURFACTANT, COMPOUNDS FOR SCREENING OUT ULTRAVIOLET RADIATION AND A CATIONIC OR ZWITTERIONIC AMPHIPHILIC COMPOUND, AND USE THEREOF

(75) Inventors: Delphine Allard, Colombes; Didier Candau, Bièvres; Luc Nicolas-Morgantini, Rully, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/486,240
(22) PCT Filed: Jul. 5, 1999
(86) PCT No.: PCT/FR99/01608
§ 371 Date: Feb. 24, 2000
§ 102(e) Date: Feb. 24, 2000
(87) PCT Pub. No.: WO00/02529
PCT Pub. Date: Jan. 20, 2000

(30) Foreign Application Priority Data
Jul. 9, 1998 (FR) .............................. 98 08828

(51) Int. Cl.[7] .............................. A61K 7/42; A61K 7/44; A61K 7/06; A61K 7/075; A61K 7/08
(52) U.S. Cl. .................. 424/59; 424/60; 424/70.1; 424/70.9; 424/70.19; 424/70.21; 424/70.22; 424/70.27; 424/70.31; 424/400; 424/401; 514/937
(58) Field of Search ................ 424/400, 401, 424/59, 60, 70.1, 70.9, 70.19, 70.21, 70.22, 70.27, 70.31; 514/937

(56) References Cited
U.S. PATENT DOCUMENTS 4,970,216 A 11/1990 Deckner et al.
5,045,307 A 9/1991 Marschner et al.
5,348,736 A 9/1994 Patel et al.
5,427,771 A * 6/1995 Grollier et al. ............... 424/59
5,658,555 A * 8/1997 Ascione et al. ............... 424/59
5,866,148 A * 2/1999 Hansenne et al. .......... 424/401

FOREIGN PATENT DOCUMENTS

EP 0 386 898 9/1990
EP 0 603 080 6/1994
WO WO 97 28785 8/1997

OTHER PUBLICATIONS

Database Chemical Abstracts Online STN, Mar. 15, 1994, XP002102399; JP 06072830 A (Lion Corp) Mar. 15, 1994; AN 121:65; 297.

* cited by examiner

Primary Examiner—Jose' G. Dees
Assistant Examiner—Marina Lamm
(74) Attorney, Agent, or Firm—Nixon & Vanderhye P.C.

(57) ABSTRACT

The invention relates to a cosmetic composition, in particular for photoprotecting the skin and/or the hair, in the form of a dispersion comprising two immiscible phases stabilized with at least one anionic surfactant chosen from the salts of fatty acids and of monovalent or polyvalent metals, of ammonium or of organic bases, a compound for screening out ultraviolet radiation, which can be adsorbed at the interface of the said immiscible phases, derived from benzylidenecamphor and comprising at least one partially or totally neutralized sulphonic acid function, a metal oxide nanopigment coated with hydrophobic hydrocarbon-based coating agents and a cationic or zwitterionic amphiphilic compound which leads, with the anionic surfactant, to the formation of a compound capable of lowering the water/liquid paraffin interface tension at 40° C. by more than 14 $mN.m^{-1}$ for an anionic surfactant concentration of 0.1 mmol/100 g, by more than 26 $mN.m^{-1}$ for an anionic surfactant concentration of 0.5 mmol/100 g and by more than 33 $mN.m^{-1}$ for an anionic surfactant concentration of 1 mmol/100 g.

40 Claims, No Drawings

PHOTOPROTECTIVE COSMETIC COMPOSITION CONTAINING AN ANIONIC SURFACTANT, COMPOUNDS FOR SCREENING OUT ULTRAVIOLET RADIATION AND A CATIONIC OR ZWITTERIONIC AMPHIPHILIC COMPOUND, AND USE THEREOF

This application is a 371 of PCT/FR99/01/608 filed Jul. 5, 1999.

The present invention relates to a cosmetic composition for topical use which is intended more particularly for photoprotecting the skin and/or the hair against ultraviolet radiation, as well as to its use in the abovementioned cosmetic application. More particularly, the present invention relates to a photo-protective composition in the form of a dispersion comprising two immiscible phases stabilized with at least one anionic surfactant, a compound for screening out UV radiation and a cationic or zwitterionic amphiphilic compound.

It is known that light radiation with wave-lengths of between 280 nm and 400 nm permits tanning of the human epidermis, and that light rays with wave-lengths of between 280 nm and 320 nm, known as UV-B rays, cause skin burns and erythema which may be harmful to the development of a natural tan; this UV-B radiation should thus be screened out.

It is also known that UV-A rays, with wave-lengths of between 320 and 400 nm, which cause tanning of the skin, are liable to induce an adverse change in the latter, especially in the case of sensitive skin or of skin which is continually exposed to solar radiation. UV-A rays in particular cause a loss of elasticity of the skin and the appearance of wrinkles, leading to premature ageing of the skin. They promote triggering of the erythemal reaction or amplify this reaction in certain individuals and may even be the cause of phototoxic or photoallergic reactions. It is thus desirable also to screen out UV-A radiation.

Many cosmetic compositions intended for the photoprotection (UV-A and/or UV-B) of the skin have been proposed to date.

Compositions based on active compounds comprising a free or at least partially neutralized acid function, which screen out UV rays, are known in the prior art. In particular, certain sulphonic compounds are known for their good properties of screening out light radiation with wavelengths of between 280 and 400 nm and more particularly between 280 and 360 nm, their thermal stability and their photochemical stability.

However, the formulation of products with a very high sun protection factor (SPF) involves the use of large concentrations of UV screening agents, which is not desirable, either from a toxicological point of view in certain cases, or from an economic point of view. The sun protection factor (SPF) is expressed mathematically by the ratio of the irradiation time required to reach the erythema-forming threshold with the UV screening agents to the time required to reach the erythema-forming threshold without UV screening agents.

It is thus important to be able to provide novel formulation systems which improve the protection factor for the same content of screening agents and which, consequently, are able to reduce the contents of UV screening agents in formulations.

After considerable research conducted in this matter, the Applicant has discovered, surprisingly and unexpectedly, that it is possible to solve this problem and to improve the sun protection factor of screening agents by modifying the interfacial behaviour of the anionic surfactant by using a cationic or zwitterionic amphiphilic compound which leads, with the anionic surfactant, to the formation of a compound capable of lowering the water/liquid paraffin interface tension at 40° C. by more than 14 mN.m$^{-1}$ for an anionic surfactant concentration of 0.1 mmol/100 g, by more than 26 mN.m$^{-1}$ for an anionic surfactant concentration of 0.5 mmol/100 g and by more than 33 mN.m$^{-1}$ for an anionic surfactant concentration of 1 mmol/100 g.

This discovery forms the basis of the present invention.

A subject of the present invention is thus a cosmetic composition for topical use, in particular for photoprotecting the skin and/or the hair, in the form of a dispersion comprising two immiscible phases stabilized with at least one anionic surfactant chosen from the salts of fatty acids and of monovalent and polyvalent metals, of ammonium or of organic bases, a compound for screening out ultraviolet radiation, consisting of a hydrophilic screening agent-comprising at least one partially or totally neutralized sulphonic acid function, which can be adsorbed at the interface of the said immiscible phases, having the formula:

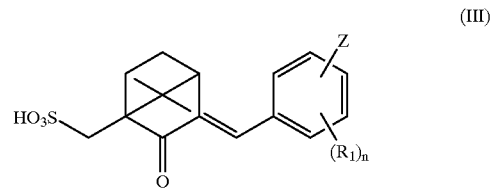

(III)

in which:

Z denotes a group of formula:

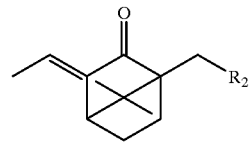

$R_2$ denoting —H or —SO$_3$H; n denotes 0 or an integer greater than or equal to 1 and less than or equal to 4;

$R_1$ represents one or more identical or different, linear or branched alkyl or alkoxy radicals containing from 1 to 4 carbon atoms, the two methylidenecamphor radicals on the phenyl ring being in a meta or para position relative to each other, as well as a metal oxide nanopigment chosen from titanium oxide, zinc oxide, iron oxide, zirconium oxide and cerium oxide, and mixtures thereof, coated with hydrophobic hydrocarbon-based coating agents, with an average primary particle size ranging from 5 to 100 nm, this composition being characterized in that it also contains a cationic or zwitterionic amphiphilic compound which leads, with the anionic surfactant, to the formation of a compound capable of lowering the water/liquid paraffin interface tension at 40° C. by more than 14 mN.m$^{-1}$ for an anionic surfactant concentration of 0.1 mmol/100 g, by more than 26 mN.m$^{-1}$ for an anionic surfactant concentration of 0.5 mmol/100 g and by more than 33 mN.m$^{-1}$ for an anionic surfactant concentration of 1 mmol/100 g.

The interface tension is measured according to Lecomte du Noüy's ring method described, for example, in Galenica, (F. Puisieux, M. Seiller), 5 Les Systèmes Dispersés, I Agents de surface et Emulsions, chapter 2, pp. 86–89.

The cationic or zwitterionic amphiphilic compound can be chosen from the compounds of formula:

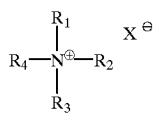

in which:

R$_1$ to R$_4$, which may be identical or different, represent a linear or branched C$_1$–C$_{30}$ alkyl, hydroxy-alkyl, alkylcarboxylate, alkylsulphonate, hydroxyalkyl-sulphonate, cycloalkyl, alkenyl, aryl or arylalkyl radical which can be interrupted with one or more hetero atoms such as oxygen or sulphur or with an —NH— or amide —CONH— group, or R$_1$ and R$_2$ and/or R$_3$ and R$_4$ form, together with the nitrogen atom to which they are attached, a five-or six-membered saturated or unsaturated heterocycle which is unsubstituted or substituted with C$_1$–C$_{30}$ alkyl, hydroxyalkyl, alkenyl, aryl or arylalkyl radicals, at least one of the radicals R$_1$ to R$_4$ or substituents on the heterocycle, and preferably at least two of these radicals or substituents, comprising at least 6 carbon atoms; X$^-$ represents an inorganic or organic ion chosen from halide, sulphate, bisulphate, methosulphate, para-toluenesulphonate and saccharinate ions, preferably chloride or bromide; it being understood that when at least one of the radicals R$_1$ to R$_4$ represents an alkylcarboxylate, alkylsulphonate or hydroxyalkyl-sulphonate radical, the ion X$^-$ does not exist.

The cationic or zwitterionic amphiphilic compound can also have the formula (II) below:

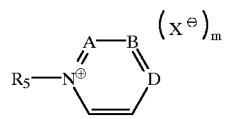

in which

R$_5$ represents a linear or branched C$_1$–C$_{30}$ alkyl, hydroxyalkyl, alkylcarboxylate, cycloalkyl, alkenyl, aryl or arylalkyl radical which can be interrupted with one or more hetero atoms such as oxygen or sulphur or with an —NH— or amide —CONH—group;

A, B or D represents CH, N, N$^+$R$_6$, R$_6$ representing a hydrogen atom, a substituted or unsubstituted, linear or branched, saturated or unsaturated C$_1$–C$_{30}$ alkyl radical which can be interrupted with one or more hetero atoms, it being understood that only one of the symbols A, B or D represents N or N$^+$R$_6$; with the proviso that at least one of the radicals R$_5$ or R$_6$ comprises at least 6 carbon atoms;

X$^-$ represents an inorganic or organic ion chosen from halide, sulphate, bisulphate, methosulphate, para-toluenesulphonate and saccharinate ions, preferably chloride or bromide;

m=0, 1 or 2.

The radicals R$_1$ to R$_6$ comprising at least 6 carbon atoms are preferably C$_8$–C$_{22}$ radicals.

The cationic or zwitterionic amphiphilic compound of formula (I) is preferably chosen from betaines such as decyl betaine, lauryl betaine, lauramidopropyl betaine, myristyl betaine, myristamidopropyl betaine, coco-betaine, cocoamidoethyl betaine, cocoamidopropyl betaine, cetyl betaine, palmamidopropyl betaine, palmitamidopropyl betaine, ricinoleamidopropyl betaine, stearamidopropyl betaine, stearyl betaine, oleyl betaine, oleamidopropyl betaine, or behenyl betaine, sultaines such as lauryl sultaine, lauryl hydroxysultaine, coco-sultaine, coco-hydroxysultaine, cocoamidopropyl hydroxysultaine or oleamidopropyl hydroxysultaine, alkyltrimethylammonium salts such as dodecyltrimethylammonium bromide or chloride, cocotrimethylammonium chloride, cetyltrimethylammonium chloride, bromide, methosulphate or tosylate, (hydrogenated) trimethylammonium tallow chloride, stearyltrimethylammonium chloride, octyldodecyltrimethylammonium chloride, behenyltrimethylammonium chloride or methosulphate or benzalkonium chloride, bromide or saccharinate, cetalkonium chloride, cetearalkonium bromide, lauralkonium chloride or bromide, stearalkonium chloride, olealkonium chloride, behenalkonium chloride and cocoylbenzylhydroxyethylimidazolinium chloride.

The cationic or zwitterionic amphiphilic compound of formula (II) is preferably chosen from cetylpyridinium chloride and laurylpyridinium chloride.

As cationic or zwitterionic amphiphilic compounds which can be used according to the invention, mention may be made more particularly of betaines.

The cationic or zwitterionic amphiphilic compound is used in concentrations ranging from 0.1 to 15% by weight of active material, and preferably from 0.1 to 10% by weight of active material, relative to the total weight of the composition.

One compound of formula (III) which is particularly preferred is the one corresponding to n=0: benzene-1,4-bis (3-methylidene-10-camphorsulphonic acid).

Hydroxides of monovalent or polyvalent metals, aqueous ammonia or organic bases such as alkylamines or alkanolamines can be used to neutralize the acid function of the abovementioned screening agents of formula (III).

The screening compounds of formula (III) used in the compositions of the invention are present in concentrations ranging from 0.1 to 20% by weight of active material relative to the total weight of the composition, more particularly from 0.2 to 10% by weight of active material and preferably from 0.5 to 5% by weight of active material.

The metal oxide nanopigments used according to the invention preferably have an average primary particle size ranging from 10 to 50 nm.

A titanium oxide nanopigment which is amorphous or crystallized in rutile and/or anatase form is preferably used.

The hydrophobic hydrocarbon-based coating on the nanopigment preferably comprises a fatty acid or a salt of a fatty acid and of a monovalent or polyvalent metal, of ammonium or of an organic base.

One nanopigment which is particularly preferred is the titanium oxide nanopigment coated with alumina and aluminium stearate, sold under the name "Microtitanium Dioxide MT-100 T" or "MT-100 TV" by the company Tayca, or the rutile titanium oxide nanopigment coated with stearic acid, sold under the name "TTO-S4" by the company Ishihara Sangyo.

The metal oxide nanopigment is present in the photoprotective composition according to the invention in a proportion of from 0.1 to 15% by weight, and preferably from 0.5 to 10% by weight, relative to the total weight of the composition.

The anionic surfactants are present in concentrations preferably ranging from 0.5 to 10% by weight of active material relative to the total weight of the composition, and more particularly from 0.5 to 5% of active material.

The composition according to the invention can also contain at least one nonionic surfactant, chosen from compounds containing an ester bond, such as glycol esters of fatty acids, glycerol esters of fatty acids, polyglycerol esters of fatty acids, tetritol, pentitol and hexitol esters of fatty acids, polyethylene glycol esters of fatty acids, sucrose esters of fatty acids, sucrose esters of triglycerides, sorbitan esters of fatty acids and polyoxyethylenated sorbitan esters or polysorbates, the compounds containing an ether bond, such as polyoxyethylene glycol alkylphenyl ethers and polyoxyethylene glycol fatty alkyl ethers, compounds containing an amide bond, such as polyoxyethylenated alkylamides and alkylene oxide copolymers.

The nonionic surfactants can be present in concentrations ranging from 0.5 to 5% by weight of active material relative to the total weight of the composition, and more particularly from 1 to 3% by weight of active material.

The cosmetic compositions according to the invention can contain one or more additional hydrophilic or lipophilic sunscreens that are active in the UV-A and/or UV-B range other than, needless to say, the screening agents defined above.

These additional screening agents can be chosen in particular from cinnamic derivatives, salicylic derivatives, camphor derivatives, triazine derivatives such as those described in patent applications EP-A-863 145, EP-A-517 104, EP-A-570 838, EP-A-796 851, EP-A-775 698 and EP-A-878 469, benzophenone derivatives, dibenzoylmethane derivatives, ββ'-diphenylacrylate derivatives, benzimidazole derivatives, bis(benzotriazolylphenol) derivatives as described in patent applications GB-A-2 303 549, DE-A-19726184 and EP-A-893 119, p-aminobenzoic acid derivatives, the screening polymers and screening silicones described in patent application WO-93/04665, and compounds comprising at least two benzazolyl groups, as described in patent application EP-A-669 323.

As examples of additional sunscreens that are active in the UV-A and/or UV-B range, mention may be made of:

p-aminobenzoic acid,
oxyethylenated (25 mol) p-aminobenzoate,
2-ethylhexyl p-dimethylaminobenzoate,
N-oxypropylenated ethyl p-aminobenzoate,
glyceryl p-aminobenzoate,
homomenthyl salicylate,
2-ethylhexyl salicylate,
triethanolamine salicylate,
4-isopropylbenzyl salicylate,
4-tert-butyl-4'-methoxydibenzoylmethane,
4-isopropyldibenzoylmethane,
2-ethylhexyl 4-methoxycinnamate,
methyl diisopropylcinnamate,
isoamyl 4-methoxycinnamate,
diethanolamine 4-methoxycinnamate,
menthyl anthranilate,
2-ethylhexyl 2-cyano-3,3'-diphenylacrylate,
ethyl 2-cyano-3,3'-diphenylacrylate,
2-phenylbenzimidazole-5-sulphonic acid and its salts,
3-(4'-trimethylammo)benzylidene-2-bornanone methyl sulphate,
2-hydroxy-4-methoxybenzophenone,
2-hydroxy-4-methoxybenzophenone-5-sulphonate,
2,4-dihydroxybenzophenone,
2,2',4,4'-tetrahydroxybenzophenone,
2,2'-dihydroxy-4,4'-dimethoxybenzophenone,
2-hydroxy-4-n-octoxybenzophenone,
2-hydroxy-4-methoxy-4'-methylbenzophenone,
α-(2-oxo-3-bornylidene)-4-tolylsulphonic acid and its salts,
3-(4'-sulpho)benzylidene-2-bornanone and its salts,
3-(4'-methylbenzylidene)-d,l-camphor,
3-benzylidene-d,l-camphor, urocanic acid,
2,4,6-tris[p-(2'-ethylhexyl-1'-oxycarbonyl)anilino]-1,3,5-triazine,
2-[(p-tert-butylamido)anilino]-4,6-bis[(p-2'-ethylhexyl-1'-oxycarbonyl)anilino]-1,3,5-triazine,
2,4-bis{[4-(2-ethylhexyloxy)-2-hydroxy]phenyl}-6-(4-methoxyphenyl)-1,3,5-triazine,
the polymer of N-(2 and 4)-[(2-oxo-3-bornylidene)methyl)benzyl]acrylamide,
polyorganosiloxanes containing a malonate function,
1,4-bis(benzimidazolyl)phenylene-3,3',5,5'-tetrasulphonic acid and its salts,
2,2'-methylenebis[6-(2H-benzotriazol-2-yl)-4-(1,1,3,3-tetramethylbutyl)phenol], sold under the name MIXXIM BB/100 by the company Fairmount Chemical.

The compositions according to the invention can also contain agents for artificially tanning and/or browning the skin (self-tanning agents), such as, for example, dihydroxyacetone (DHA).

The compositions of the invention can also comprise cosmetic adjuvants chosen in particular from fatty substances, organic solvents, ionic or nonionic thickeners and/or gelling agents, softeners, anti-oxidants, opacifiers, stabilizers, emollients, hydroxy acids, vitamins, hydrophilic or lipophilic active agents such as ceramides, reducing agents, silicones, free-radical scavengers, antifoaming agents, hydrating agents, fragrances, preserving agents, fillers, sequestering agents, polymers, propellants, acidifying or basifying agents, dyes or any other ingredient usually used in cosmetics.

The fatty substances can consist of an oil or a wax or a mixture thereof, petroleum jelly, paraffin, lanolin, hydrogenated lanolin or acetylated lanolin; they also comprise fatty acids, fatty alcohols such as lauryl alcohol, cetyl alcohol, myristyl alcohol, stearyl alcohol, palmityl alcohol, oleyl alcohol and 2-octyldodecanol, fatty acid esters such as glyceryl monostearate, polyethylene glycol monostearate, isopropyl myristate, isopropyladipate, isopropyl-palmitate, octylpalmitate, $C_{12}$–$C_{15}$ fatty alkylbenzoates (Finsolv TN from Finetex), myristyl alcohol polyoxy-propylenated with 3 mol of propylene oxide (Witconol APM from Witco), and $C_6$–$C_{18}$ fatty acid triglycerides such as caprylic/capric acid triglycerides.

The oils are chosen from animal, plant, mineral or synthetic oils, and in particular hydrogenated palm oil, hydrogenated castor oil, liquid petroleum jelly, liquid paraffin, purcellin oil (stearyl octanoate), silicone oils and isoparaffins.

The waxes are chosen from animal, fossil, plant, mineral and synthetic waxes. Mention may be made in particular of beeswaxes, carnauba wax, candelilla wax, sugar cane wax, Japan wax, ozokerites, Montan wax, microcrystalline waxes, paraffins and silicone waxes and resins.

Among the organic solvents which may be mentioned are lower alcohols and polyalcohols such as ethanol, isopropanol, propylene glycol, glycerol and sorbitol.

The thickeners and/or gelling agents can be chosen from crosslinked polyacrylic acids, modified or unmodified guar gums or cellulose gums, such as hydroxypropyl guar gum, methylhydroxyethylcellulose, cetylhydroxyethylcellulose, hydroxypropylmethylcellulose or hydroxyethylcellulose, and silicas such as, for example, Bentone Gel Mio sold by the company NL Industries or Veegum Ultra sold by the company Polyplastic.

Needless to say, a person skilled in the art will take care to select this or these optional additional compound(s) and/or the amounts thereof such that the advantageous properties intrinsically associated with the photoprotective composition in accordance with the invention, in particular the protection factor, are not, or are not substantially, adversely affected by the addition(s) envisaged.

The cosmetic composition of the invention can be used as a composition for protecting the human epidermis or the hair against ultraviolet rays, as an antisun composition or as a make-up product.

This composition can be in particular in the form of a simple or complex emulsion (O/W, W/O, O/W/O or W/O/W), such as a cream, a milk or a cream-gel, or in the form of a powder or a solid tube and can optionally be packaged as an aerosol and can be in the form of a foam or a spray.

The compositions according to the invention can be prepared according to the techniques which are well known to those skilled in the art, in particular those intended for the preparation of oil-in-water or water-in-oil emulsions.

When it is an emulsion, the aqueous phase of this emulsion can comprise a nonionic vesicle dispersion prepared according to known processes (Bangham, Standish and Watkins, J. Mol. Biol. 13, 238 (1965), FR-A-2,315,991 and FR-A-2,416,008).

Another subject of the present invention is a non-therapeutic process for treating the skin or the hair which is intended to protect them against the effects of UV rays, this process consisting in applying an effective amount of a cosmetic composition as defined above to the skin or the hair.

When the cosmetic composition according to the invention is used for protecting the human epidermis against UV rays or as an antisun composition, it can be in the form of a dispersion in solvents or fatty substances, in the form of a nonionic vesicle dispersion or in the form of an emulsion such as a cream, a milk or a cream-gel or in the form of a solid tube, and can be packaged as an aerosol and be in the form of a foam or spray.

When the cosmetic composition according to the invention is used for protecting the hair, it can be in the form of a shampoo, an emulsion or a nonionic vesicle dispersion, it can be packaged as an aerosol and can be in the form of a foam or spray; it can constitute, for example, a rinse-out composition, to be applied before or after shampooing, before or after dyeing or bleaching or before, during or after permanent-waving or straightening the hair, or a composition for permanent-waving, straightening, dyeing or bleaching the hair.

When the composition is used as a make-up product for the eyelashes, the eyebrows or the skin, such as an epidermal conditioning cream, a foundation, a tube of lipstick, an eyeshadow, a face powder, a mascara or an eyeliner, it can be in liquid, solid or pasty, anhydrous or aqueous form, such as simple or multiple emulsions or alternatively nonionic vesicle dispersions, powders or solid tubes.

As a guide, for the antisun formulations in accordance with the invention which contain a support of oil-in-water emulsion type, the aqueous phase (in particular comprising the hydrophilic screening agents) generally represents from 50 to 95% by weight, preferably from 70 to 90% by weight, relative to the formulation as a whole and the oily phase (in particular comprising the lipophilic screening agents) represents from 5 to 50% by weight, preferably from 10 to 30% by weight, relative to the formulation as a whole.

The invention will be better illustrated by means of the examples below.

EXAMPLE 1

An antisun composition in accordance with the invention was prepared in the form of an emulsion of oil-in-water type, containing the constituents below, whose proportions are expressed as a percentage by weight relative to the total weight of the composition:

| | | |
|---|---|---|
| Mixture of glyceryl stearate and of polyethylene glycol stearate containing 100 mol of ethylene oxide, sold under the name "Arlacel 165" by the company ICI | | 2% |
| Stearic acid | | 2.5% |
| Cetyl alcohol | | 0.5% |
| Silicone gum: α,ω-dihydroxylated polydimethylsiloxane in cyclomethicone, sold under the name DC-2-9071 by the company Dow Corning | | |
| Fatty acid triglycerides | | 4% |
| Isoparaffin | | 3% |
| Karite butter | | 1.5% |
| Jojoba oil | | 1.5% |
| Titanium oxide nanopigment sold under the name "Microtitanium dioxide MT-100T" by the company Tayca | | 5% |
| 2-Ethylhexyl 2-cyano-3,3-diphenyl acrylate sold under the name "Uvinui N-539" by the company BASF | | 10% |
| 4-tert-Butyl-4'-methoxydibenzoylmethane sold under the name "Parsol 1789" by the company Roche | | 2% |
| Glycerol | | 4% |
| Propylene glycol | | 4% |
| Benzene-1,4-bis(3-methylidene-10-camphorsulphonic acid) | | 0.5% AM |
| Coco-betaine | | 2% AM |
| Acrylic acid/($C_{10}$-$C_{30}$) alkyl acrylate crosslinked copolymer sold under the name "Pemulen TR1" by the company Goodrich | | 0.12% |
| Hydroxypropylmethylcellulose | | 0.1% |
| Triethanolamine | | 0.83% |
| Preserving agents | qs | |
| Fragrance | qs | |
| Demineralized water | qs | 100% |

The compartive compositions A and B of the same composition as that above were also prepared, composition A containing the liposoluble UV screening agents, the screening agent containing an acid function and the nanopigment, but not containing the zwitterionic amphiphilic coco-betaine compound, and composition B containing only the zwitterionic amphiphilic coco-betaine compound, but not containing screening agents or nanopigment.

Each of these emulsions was prepared by dissolving the liposoluble UV screening agents in the fatty phase, then adding the emulsifiers to this fatty phase brought to about 80° C., and finally adding, with rapid stirring, the aqueous phase containing the benzene-1,4-bis(3-methylidene-10-camphorsulphonic acid) neutralized with triethanolamine, the aqueous phase being preheated to this same temperature.

EXAMPLE 2

An antisun composition in accordance with the invention was prepared, replacing the coco-betaine with lauramidopropyl betaine used at the same concentration.

EXAMPLE 3

The betaines of Examples 1 and 2 were replaced with dodecyltrimethylammonium chloride, used at the same concentration.

For each of the formulations thus prepared, the sun protection factor associated therewith was then determined. This was determined using the in vitro method described by B. L. Diffey et al. in J. Soc. Cosmet. Chem. 40-127–133 (1989); this method consists in determining the monochromatic protection factors every 5 nm over a wavelength range from 290 to 400 nm and in calculating the protection factor therefrom according to a given mathematical equation.

The average sun protection factor calculated from three measured values and the standard deviation are given in the table below.

|  | Example 1 | Comparative Example A | Comparative Example B | Example 2 | Example 3 |
|---|---|---|---|---|---|
| Average SPF (standard deviation) | 31.9 (6.6) | 16.8 (0.1) | 1 | 33 (3) | 27.7 (7.4) |

These results clearly show that, for the same photoprotective system, i.e. nanopigment +liposoluble UV screening agents+benzene-1,4-bis(3-methylidene-10-camphorsulphonic acid), the composition of Example 1 according to the invention containing the amphiphilic zwitterionic coco-betaine compound has a significantly higher sun protection factor than that of the Comparative Example A, although the amphiphilic zwitterionic compound itself has no photoprotective power (see Comparative Example B).

These results were confirmed by the in vivo method which consists in applying the formulations, at a rate of 2 mg of product/cm² of skin, onto the back of 5 human subjects and then simultaneously subjecting the protected zones and unprotected zones of skin to the action of a Xenon Multiport WG 320-1 mm+UG 11-1 mm sun simulator.

The results are as follows:

|  | Comparative Example A | Example 1 | Example 2 | Example 3 |
|---|---|---|---|---|
| Average SPF (standard deviation) | 22.5 (5.5) | 41.4 (12.1) | 32.2 (3.3) | 28.7 (5) |

What is claimed is:

1. A cosmetic composition for topical use in the form of a dispersion comprising two immiscible phases stabilized with at least one anionic surfactant selected from the group consisting of a salt of a fatty acid, with a monovalent or polyvalent metal, an ammonium base or an organic base; and a hydrophilic ultraviolet radiation screening agent comprising at least one partially or totally neutralized sulphonic acid function, which can be adsorbed at the interface of the said immiscible phases, having the formula:

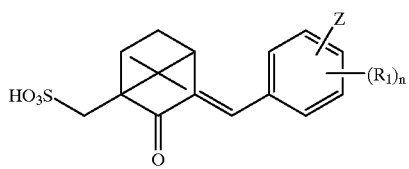

(III)

in which:
Z denotes a group of formula:

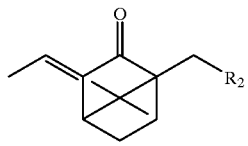

wherein $R_2$ is —H or —SO$_3$H;
n is 0 or an integer greater than or equal to 1 and less than or equal to 4;
$R_1$ represents one or more identical or different, linear or branched alkyl or alkoxy radicals containing from 1 to 4 carbon atoms,
the two methylidenecamphor radicals on the phenyl ring being in a meta or para position relative to each other,
said composition further comprising a metal oxide nanopigment selected from the group consisting of a titanium oxide nanopigment, a zinc oxide nanopigment, an iron oxide nanopigment, a zirconium oxide nanopigment, a cerium oxide nanopigment, and mixtures thereof, said nanopigment being coated with a hydrophobic hydrocarbon-based coating agent and having an average primary particle size ranging from 5 to 100 nm, the composition further comprising a cationic or zwitterionic amphiphilic compound which leads, with the anionic surfactant, to the formation of a compound capable of lowering the water/liquid paraffin interface tension at 40° C. by more than 14 mN.m$^{-1}$ for an anionic surfactant concentration of 0.1 mmol/100 g, by more than 26 mN.m$^{-1}$ for an anionic surfactant concentration of 0.5 mmol/100 g and by more than 33 mN.m$^{-1}$ for an anionic surfactant concentration of 1 mmol/100 g.

2. A composition according to claim 1, wherein the cationic or zwitterionic amphiphilic compound has the formula:

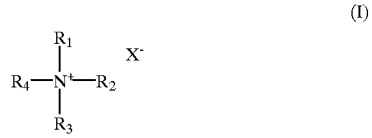

(I)

in which:
$R_1$ to $R_4$, which may be identical or different, represent a linear or branched $C_1$–$C_{30}$ alkyl, hydroxyalkyl, alkylcarboxylate, alkylsulphonate, hydroxyalkylsulphonate, cycloalkyl, alkenyl, aryl or arylalkyl radical which can be interrupted with one or more hetero atoms or with an —NH— or —CONH— group, or $R_1$ and $R_2$ and/or $R_3$ and $R_4$ form, together with the nitrogen atom to which they are attached, a five- or six-membered saturated or unsaturated heterocycle which is unsubstituted or substituted with $C_1$–$C_{30}$ alkyl, hydroxyalkyl, alkenyl, aryl or arylalkyl radicals, at least one of the radicals $R_1$ to $R_4$ or substituents on the heterocycle, comprising at least 6 carbon atoms;

$X^-$ is an inorganic or organic ion selected from the group consisting of a halide ion, a sulphate ion, a bisulphate ion, a methosulphate ion, a paratoluenesulphonate ion and a saccharinate ion; it being understood that when at least one of the radicals $R_1$ to $R_4$ represents an alkylcarboxylate, alkylsulphonate or hydroxyalkylsulphonate radical, the ion $X^-$ does not exist.

3. A composition of claim 2, wherein said hetero atoms are oxygen or sulphur.

4. A composition of claim 2 wherein at least two of $R_1$ to $R_4$ or substituents on the heterocycle comprise at least 6 carbon atoms.

5. A composition of claim 2 wherein said halide ion is a chloride ion or a bromide ion.

6. A composition according to claim 1, wherein the cationic or zwitterionic amphiphilic compound has the formula:

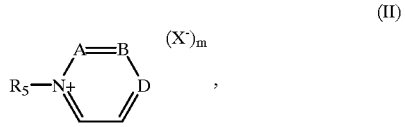

(II)

in which:

$R_5$ is a linear or branched $C_1$–$C_{30}$ alkyl, hydroxyalkyl, alkylcarboxylate, cycloalkyl, alkenyl, aryl or arylalkyl radical which can be interrupted with one or more hetero atoms or with a —NH— or —CONH— group;

A, B or D represents CH, N, and $N^+R_6$, $R_6$ representing a hydrogen atom, a substituted or unsubstituted, linear or branched, saturated or unsaturated $C_1$–$C_{30}$ alkyl radical which can be interrupted with one or more hetero atoms, it being understood that only one of the symbols A, B or D represents N or $N^+R_6$;

with the proviso that at least one of the radicals $R_5$ or $R_6$ comprises at least 6 carbon atoms;

$X^-$ represents an inorganic or organic ion selected from the group consisting of a halide ion, a sulphate ion, a bisulphate ion, a methosulphate ion, a paratoluenesulphonate ion and a saccharinate ion; and m =0, 1 or 2.

7. A composition of claim 6 wherein said hetero atoms are oxygen or sulphur.

8. A composition of claim 6 wherein said halide ion is a chloride ion or a bromide ion.

9. A composition according to claim 2 wherein said at least one of $R_1$ to $R_4$ or substituents on the heterocycle comprise a $C_8$–$C_{22}$ radical.

10. A composition according to claim 6 wherein said at least one of $R_5$ or $R_6$ comprises a $C_8$–$C_{22}$ radical.

11. A composition according to claim 2 wherein the compound of formula (I) is selected from the group consisting of decyl betaine, lauryl betaine, lauramidopropyl betaine, myristyl betaine, myristamidopropyl betaine, cocobetaine, cocoamidoethyl betaine, cocoamidopropyl betaine, cetyl betaine, palmamidopropyl betaine, palmitamidopropyl betaine, ricinoleamidopropyl betaine, stearamidopropyl betaine, stearyl betaine, oleyl betaine, oleamidopropyl betaine, behenyl betaine, lauryl sultaine, lauryl hydroxysultaine, coco-sultaine, coco-hydroxysultaine, cocoamidopropyl hydroxysultaine, oleamidopropyl hydroxysultaine, dodecyltrimethylammonium bromide or chloride, cocotrimethylammonium chloride, cetyltrimethylammonium chloride, bromide, methosulphate or tosylate, (hydrogenated) trimethylammonium tallow chloride, stearyltrimethylammonium chloride, octyldodecyltrimethylammonium chloride, behenyltrimethylammonium chloride or methosulphate or benzalkonium chloride, bromide or saccharinate, cetalkonium chloride, cetearalkonium bromide, lauralkonium chloride or bromide, stearalkonium chloride, olealkonium chloride, behenalkonium chloride and cocoylbenzylhydroxyethylimidazolinium chloride.

12. A composition according to claim 1 wherein the cationic or zwitterionic amphiphilic compound of formula (II) is cetylpyridinium chloride or laurylpyridinium chloride.

13. A composition according to claim 1 wherein the cationic or zwitterionic amphiphilic compound is present in a concentration ranging from 0.1 to 15% by weight of active material, relative to the total weight of the composition.

14. A composition of claim 13 wherein said concentration ranges from 0.1 to 10% by weight active material.

15. A composition according to claim 1 wherein the compound of formula (III) is benzene-1,4-bis(3-methylidene-10-camphorsulphonic acid).

16. A composition according to claim 1 wherein the sulphonic acid function of the compound of formula (III), is neutralized with a compound selected from the group consisting of a monovalent metal hydroxide, a multivalent metal hydroxide, aqueous ammonia and an organic base.

17. A composition according to claim 1 wherein the compound of formula (III) is present in a concentration ranging from 0.1 to 10% by weight of active material relative to the total weight of the composition.

18. A composition of claim 17 wherein said concentration ranges from 0.2 to 8% by weight of active material.

19. A composition of claim 17 wherein said concentration ranges from 0.5 to 5% by weight of active material.

20. A composition according to claim 1 wherein the anionic surfactant is present in concentrations ranging from 0.5 to 10% by weight of active material relative to the total weight of the composition.

21. A composition according to clam 20 wherein said concentration ranges from 0.5 to 5% by weight of active material.

22. A composition according to claim 1 wherein the metal oxide nanopigment is a titanium oxide nanopigment.

23. A composition according to claim 1 wherein the hydrophobic hydrocarbon-based coating agent comprises a fatty acid, a salt of a fatty acid and of a monovalent metal, a salt of a fatty acid and a multivalent metal, a salt of a fatty acid and ammonium or a salt of a fatty acid and an organic base.

24. A composition according to claim 1 wherein the metal oxide nanopigment has an average primary particle size ranging from 10 to 50 nm.

25. A composition according to claim 1 wherein the metal oxide nanopigment is present in a proportion of from 0.1 to 15% by weight relative to the total weight of the composition.

26. A composition according to claim 25 wherein the nanopigment is present in a proportion of from 0.5 to 10% by weight.

27. A composition according to claim 1, further comprising at least one nonionic surfactant selected from the group consisting of a compound containing an ester bond, a compound containing an ether bond, and a compound containing an amide bond.

28. A composition of claim 27 wherein said at least one non-ionic surfactant is selected from the group consisting of a fatty acid ester of a glycol, a fatty acid ester of glycerol, a fatty acid ester of a polyglycerol, a fatty acid ester of tetritol, pentitol or hexitol, a fatty acid ester of a polyethylene glycol, a fatty acid ester of sucrose, a triglyceride ester of sucrose, a fatty acid ester of sorbitan, a polyoxyethylenated sorbitan ester, a polysorbate, a polyoxyethylene glycol alkylphenyl ether, a polyoxyethylene glycol fatty alkyl ether, a polyoxyethylenated alkylamide and a alkylene oxide copolymer.

29. A composition according to claim 27, wherein the at least one nonionic surfactant is present in a concentration ranging from 0.5 to 5% by weight of active material relative to the total weight of the composition.

30. A composition of claim 29 wherein said concentration ranges from 1 to 3% by weight of active material.

31. A composition according to claim 1, further comprising one or more additional hydrophilic or lipophilic UV-B and/or UV-A sunscreens.

32. A composition according to claim 31, wherein the additional sunscreen is selected from the group consisting of a cinnamate, a salicylate, a benzylidenecamphor derivative, a triazine derivative, a benzophenone derivative, a dibenzoylmethane derivative, a β, β'-diphenyl acrylate derivative, a p-aminobenzoic acid derivative, a benzimidazole derivative, a bis(benzotriazolylphenol) derivative, a screening polymer, a screening silicone, and a compound comprising at least two benzazolyl groups.

33. A composition according to claim 1, further comprising at least one cosmetic adjuvant selected from the group consisting of a fatty substance, an organic solvent, an ionic thickener, a nonionic thickener, a gelling agent, a softener, an antioxidant, an opacifier, a stabilizer, an emollient, a hydroxy acid, a vitamin, a hydrophilic active agent, a lipophilic active agent, a reducing agent, a silicone, a free-radical scavenger, an antifoaming agent, a hydrating agent, a fragrance, a preserving agent, a filler, a sequestering agent, a polymer, a propellant, an acidifying agent, a basifying agent and a dye.

34. A composition according to claim 1, which constitutes a composition for protecting the human epidermis against UV rays or an antisun composition and is in the form of a dispersion, an emulsion, a solid stick, a foam or a spray.

35. A composition of claim 34, which is in the form of a cream, milk or cream-gel.

36. A composition according to claim 1, which constitutes a make-up composition for the eyelashes, the eyebrows or the skin and is in the form of a solid, a liquid or a paste.

37. A composition according to claim 36, in the form of an emulsion, a nonionic vesicle dispersion, a powder or a solid stick.

38. A composition according to claim 1 for protecting hair against UV rays, which is in the form of a shampoo, an emulsion, a nonionic vesicle dispersion, a foam or a spray.

39. A non-therapeutic process for treating at least one of the skin and the hair to protect said skin or hair against the effects of UV rays with wavelengths of between 280 and 400 nm, said process comprising applying an effective amount of a photoprotective cosmetic composition comprising a composition according to claim 1.

40. A method of increasing the sun protection factor of a cosmetic composition for topical use in the form of a dispersion comprising two immiscible phases stabilized with at least one anionic surfactant selected from the group consisting of a salt of a fatty acid, with a monovalent or polyvalent metal, an ammonium base or an organic base; and a hydrophilic ultraviolet radiation screening agent comprising at least one partially or totally neutralized sulphonic acid function, which can be adsorbed at the interface of the said immiscible phases, having the formula:

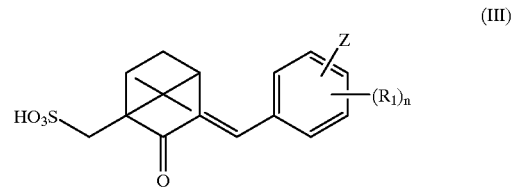

(III)

in which:

Z denotes a group of formula:

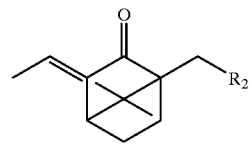

wherein $R_2$ is —H or —$SO_3H$;

n is 0 or an integer greater than or equal to 1 and less than or equal to 4;

$R_1$ represents one or more identical or different, linear or branched alkyl or alkoxy radicals containing from 1 to 4 carbon atoms, the two methylidenecamphor radicals on the phenyl ring being in a meta or para position relative to each other, said composition further comprising a metal oxide nanopigment selected from the group consisting of a titanium oxide nanopigment, a zinc oxide nanopigment, an iron oxide nanopigment, a zirconium oxide nanopigment, a cerium oxide nanopigment, and mixtures thereof, said nanopigment being coated with a hydrophobic hydrocarbon-based coating agent and having an average primary particle size ranging from 5 to 100 nm, said method comprising adding to said cosmetic composition a cationic or zwitterionic amphilphilic compound which leads, with the anionic surfactant, to the formation of a compound capable of lowering the water/liquid paraffin interface tension at 40° C. by more than 14 mN.m$^{-1}$ for an anionic surfactant concentration of 0.1 mmol/100 g, by more than 26 mN.m$^{-1}$ for an anionic surfactant concentration of 0.5 mmol/100 g and by more than 33 mN.m$^{-1}$ for an anionic surfactant concentration of 1 mmol/100 g.

* * * * *